United States Patent [19]
Lannoye et al.

[11] Patent Number: 5,304,148
[45] Date of Patent: Apr. 19, 1994

[54] NEEDLE CAP AND SHIELD

[76] Inventors: Randy J. Lannoye; Floyd D. Lannoye, both of 12436 SE. 248th St., Kent, Wash. 98031

[21] Appl. No.: 822,621

[22] Filed: Jan. 17, 1992

[51] Int. Cl.⁵ .............................. A61M 5/32
[52] U.S. Cl. .......................... 604/192; 604/263; 128/919
[58] Field of Search ............. 604/192, 187, 263; 128/919

[56] References Cited

U.S. PATENT DOCUMENTS

| | | | |
|---|---|---|---|
| 2,972,991 | 2/1961 | Burke | 128/218 |
| 3,021,942 | 2/1962 | Hamilton | 206/43 |
| 4,559,042 | 12/1985 | Votel | 604/192 |
| 4,573,975 | 3/1986 | Frist et al. | 604/192 |
| 4,623,336 | 11/1986 | Pedicano et al. | 604/192 |
| 4,740,204 | 4/1988 | Masters et al. | 604/192 |
| 4,767,412 | 8/1988 | Haymanson | 604/192 |
| 4,781,697 | 11/1988 | Slaughter | 604/192 |
| 4,799,927 | 1/1989 | Davis et al. | 604/192 |
| 4,857,060 | 8/1989 | Rosenberg | 604/192 |
| 4,921,489 | 5/1990 | Frizzell | 604/192 |

FOREIGN PATENT DOCUMENTS 8503006  7/1985  World Int. Prop. O. .......... 604/192

OTHER PUBLICATIONS

Needle Guard Reduces Needlesticks, by Charles J. Murray, Design News, Oct. 23, 1986, pp. 120–121.

High prices May Hinder Widespread Use of Needles with New Safety Features, by Mary Wagner, Modern Healthcare, Jun. 11, 1990, p. 68.

*Primary Examiner*—John D. Yasko
*Attorney, Agent, or Firm*—R. Reams Goodloe, Jr.

[57] ABSTRACT

A needle cap and shield. An needle cap is provided with a continuous expandable shield. The shield is collapsible and thus it is capable of being easily packed and shipped. When released by the user, the shield expands into a fully protective needle shield which provides protection to the user from needle sticks. The shield does not have any voids or open areas, and is thus fully protective to the user. Also, in one embodiment, a flat edge segment is furnished; this flat edge enables the cap and shield, or a recapped syringe with cap and shield, to be securely positioned on a flat surface without danger of rolling away.

21 Claims, 4 Drawing Sheets

NEEDLE CAP AND SHIELD

TECHNICAL FIELD OF THE INVENTION

This invention relates to a novel shield for use with a needle cap to protect a user against needle stick during the re-capping of needles.

BACKGROUND OF THE INVENTION

A continuing demand exists for a simple, fully protective, and inexpensive cap and shield which can be used to reduce or eliminate needle sticks to medical personnel. Presently, medical personnel are at risk during the re-capping of a needle during use or prior to disposal. The need to reduce this risk is particularly great at this time due to the increasing threat to medical personnel of the fatal blood born disease, the AIDS or HIV virus. In addition, well known diseases such as hepatitis B or non-A non-B hepatitis continue to be a major source of occupational disease amongst medical personnel. Therefore, the need exists to provide better protection to those exposed to such risks than may be provided by devices currently available.

More specifically, an urgent need exists to produce an inexpensive, easily stored protective device which enables a needle to be recapped with minimal risk to medical personnel.

Many caps, shields, or other protective devices of the character described above which provide the general capabilities desired have heretofore been proposed. Those of which we are aware are disclosed in U.S. Pat. Nos. 2,972,991, issued Feb. 28, 1961 to Burke for DISPOSABLE SYRINGE; 3,021,942 issued Feb. 20, 1962 to Hamilton for NEEDLE PACKAGE; 4,559,042 issued Dec. 7, 1985 to Votel for SAFETY ENCLOSURE FOR DISPOSABLE HYPODERMIC SYRINGE NEEDLE; 4,573,975 issued Mar. 4, 1986 to Frist et al. for PROTECTIVE SHIELD FOR NEEDLE RECEIVER; 4,623,336 issued Nov. 18 1986 to Pedicano et al. for DISPOSABLE SAFETY NEEDLE SHEATH; 4,740,204 issued Apr. 26, 1988 to Masters et al. for SAFETY NEEDLE CAP; 4,767,412 issued Aug. 30, 1988 to Hymanson for FINGER GUARDS; 4,781,697 issued Nov. 1, 1988 to Slaughter for REMOVABLE PROTECTIVE SHIELD FOR NEEDLE SHEATH; and 4,799,927, issued Jan. 24, 1989 to Davis et al. for NEEDLE GUIDE AND PUNCTURE PROTECTOR. More generally, an article entitled "Needle Guard Reduces Needlesticks" by Charles J. Murray in Design News, Oct. 23, 1989 provides background on the basis for concern regarding effective shielding needle sticks. Also, an article entitled "High Prices may hinder widespread use of needles with new safety features" by Mary Wagner in Modern Healthcare, Jun 11, 1990, provides further background regarding safety devices currently available.

For the most part, the documents identified in the preceding paragraphs disclose devices which have one or more of the following shortcomings: (a) they are difficult to package, (b) they are unstable or metastable on flat surfaces, and (c) they are relatively expensive to manufacture.

One of the most common deficiencies of the heretofore available needle shield devices of which we are aware is the lack of packing efficiency, due the the rigid type of structure most commonly found. Even those devices which have attempted to provide some packing efficiency, particularly the Frist et al. protective shield, have resulted in undesirable voids or gaps in the protective shield, thus continuing to pose a danger to medical personnel. Thus, the advantages of the compact, collapsible, continuous (voidless), and easily manufactured design of our novel needle cap and shield are important and self-evident.

SUMMARY OF THE INVENTION

We have now invented, and disclose herein, a novel, improved needle shield which does not have the above-discussed drawbacks common to those somewhat similar products heretofore used of which we are aware. Unlike the needle caps and shields heretofore available, our product is simple, lightweight, relatively inexpensive, easy to manufacture, and otherwise superior to those heretofore used or proposed. In addition, it provides a significant, demonstrated additional measure of additional protection against unwanted needle sticks when compared to many currently known designs.

Our novel needle cap and shield includes a cap housing having a sidewall, with the cap sidewall having an interior and an exterior, and with the cap having a frontal opening adapted to receive a needle. There are a plurality of spaced panels extending upward from the exterior sidewall. The adjacent panels have interior edges therebetween, with the interior edges being shaped to define generally stiff projections or ribs which are in fact an expansion means for supporting and urging the panels out of contact with the exterior sidewall. The ribs are fabricated out of a material which has somewhat of a memory in that it tends to expand or return to the originally manufactured configuration, such as polyethylene or polypropylene. Thus, the ribs, when freed, tend to extend outward from a compressed, shipping position toward an extended, protective position. As a result, the shield is expandable upon opening to provide a large, continuous needle puncture resistant protective surface area, with the protective surface adjacent to an annular needle receiving area within the cap. The stiffening means or ribs may be integrally formed with the protective surface of the shield as well as the cap, thus forming a one piece shield and cap. Alternately, the ribs may be formed from a ring or band and thus the shield portion may be separately formed and slipped on to the cap.

Caps and shields made according to the teachings herein differ from those previously available products mentioned above in one respect in that a tough, lightweight, continuous shield is provided. When the shield is integrally manufactured with the cap, as it may well be in the preferred configuration, our needle caps with shields will provide shields comparable or lighter in weight than conventional or previously available shields. Moreover, our method of packing needle caps and shields enabling high packing densities for shipping while providing a product which is fully protective to the user.

OBJECTS, ADVANTAGES, AND FEATURES OF THE INVENTION

From the foregoing, it will be apparent to the reader that one important and primary object of the present invention resides in the provision of a novel, improved needle cap and shield to provide a means reduce the risk of needle sticks to medical personnel, thereby preventing or reducing the risk of occupational disease in medical personnel using our novel device.

Other important but more specific objects of the invention reside in the provision of needle cap and shield as described in the preceding paragraph which:
can be manufactured in a simple, straightforward manner;
results in collapsible shield which can be tightly packed for shipping purposes;
in conjunction with the preceding object, have the advantage that they can be expanded when opened by medical personnel to quickly establish an open, fully protective configuration; and
which provides a cap and shield which is easy to use and re-use; and
which provide a means for safely and reliably locating in a stationary position the needle cap and shield (with or without needle) on any flat surface.

Other important objects, features, and additional advantages of our invention will become apparent to the reader from the foregoing and the appended claims and as the ensuing detailed description and discussion proceeds in conjunction with the accompanying drawing.

BRIEF DESCRIPTION OF THE DRAWING

In the drawing:

FIG. 3A is a cross-sectional view of a needle cap while engaging a needle and syringe, similar the view first shown in FIG. 3, but with a separately manufactured shield having a ring for support of extending ribs.

DETAILED DESCRIPTION OF THE INVENTION

Figure 1:
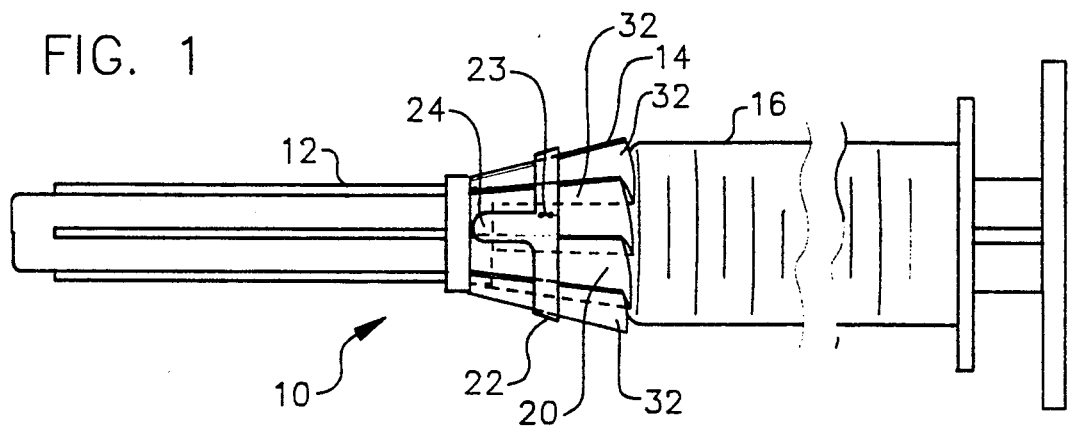
FIG. 1 is a side view of the cap and collapsible needle shield in the collapsed, shipping position, including a securing ring around the collapsed shield to hold it securely in place according to the present invention.
Figure 2:
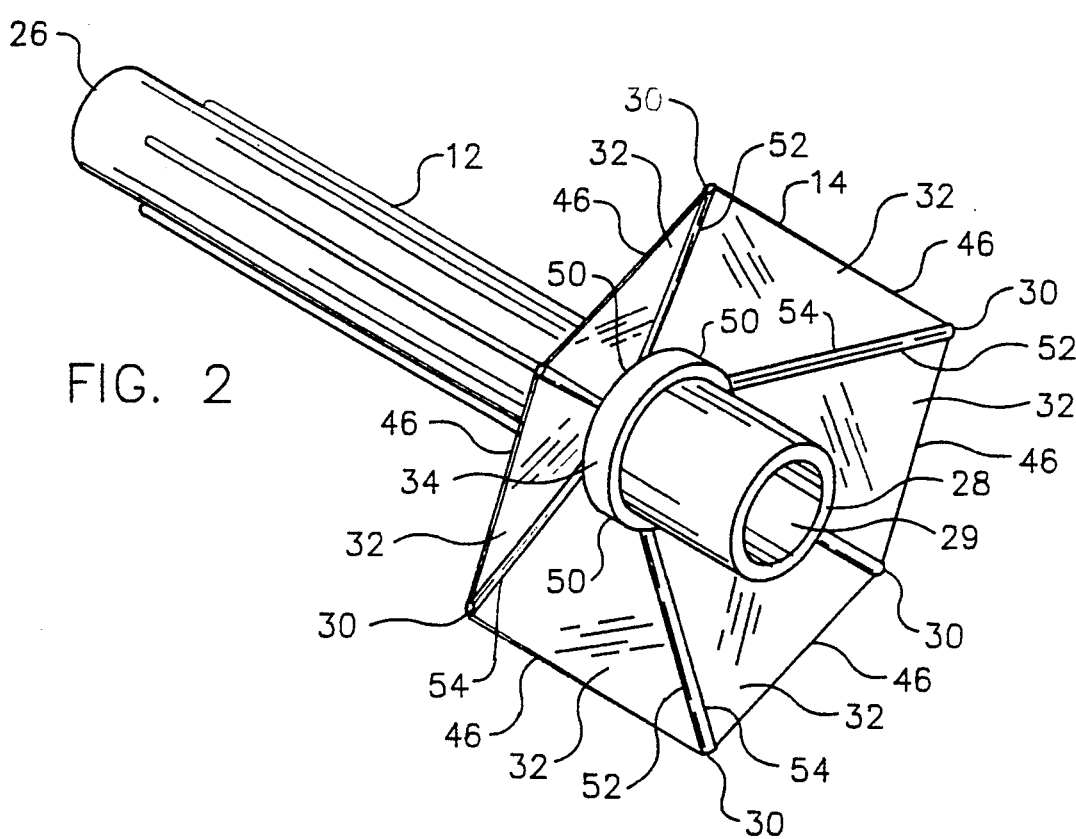
FIG. 2 is a perspective view of a cap and shield first illustrated in FIG. 1, now showing the shield in its expanded position, and revealing the stiffening ribs according to the present invention.

Turning now to FIG. 1, there is shown an article 10 of manufacture including a needle cap 12 with integral shield 14. The cap 12 has inserted therein a syringe 16 with a needle 18 (hidden in cap 12, shown in FIG. 3 below). In this FIG. the flexible, collapsible shield 14 is shown in its collapsed position 20 for storage and shipment prior to use. The shield 14 is maintained in its stored position by retaining ring 22. The retaining ring 22 may be supplied with a tab 24, which may be pulled by the user to break ring 22 at a weakened position such as perforations 23 to thereby release shield 14 for transformation into its expanded configuration as illustrated in FIG. 2. In normal medical use, it may be desirable to provide ring 22 and tab 24 in a bright or fluorescent color, so as to aid in preventing the loss of the tab during a medical procedure. As an additional aid in preventing such undesirable loss, the tab may be thermowelded to a panel or rib. Shield 14 may be made out of any suitable flexible, puncture resistant material such as polyethylene or polypropylene plastic. It is advantageous to select these materials, or materials with similar properties in that the selected materials have a natural memory, i.e., they have a tendency, to a sufficient extent for the device to perform as illustrated herein, to return to their manufactured shape even though deformed during packaging and shipping. The tab 24 may be fabricated using the same material as provided for shield 14, or alternately may be of any other suitable material with sufficient strength to securely hold shield 14 in its collapsed position 20.

It will be readily apparent to the reader that the present invention may be easily adapted to other embodiments incorporating the concepts taught herein and that the present FIG. 1 is shown by way of example only and not in any way a limitation. As to embodiments illustrated in the following figures, like parts will be noted with common reference numerals without further discussion thereof.

In FIG. 2, it can be noted that the shield 14 is integrally formed with cap 12. Cap 12 has at one end a top or closed end 26, and at the other end an annular ring 28 defining an annular opening 29 adapted to receive a needle 18 (shown in FIG. 3 below). The shield 14 is comprised of a ribs 30 and panels 32. If necessary, a central ring 34 may be provided for extra strength and memory as required to urge ribs 30 toward the expanded configuration illustrated when ribs 30 are released by the removal of ring 22. However, a ring is normally necessary only when providing an independent shield (such as is shown in FIG. 3A below), rather than when providing an integrally manufactured cap and shield, as is illustrated in FIGS. 2 and 3.

Returning now to FIG. 1, it can be seen that the panels 32 can be folded over each other, in essentially the same manner as portions of panels of an umbrella may be folded over each other after collapsing the same. In the same manner as a strap on an umbrella, the ring 22 secures the panels 32 in the collapsed position.

Figure 3:
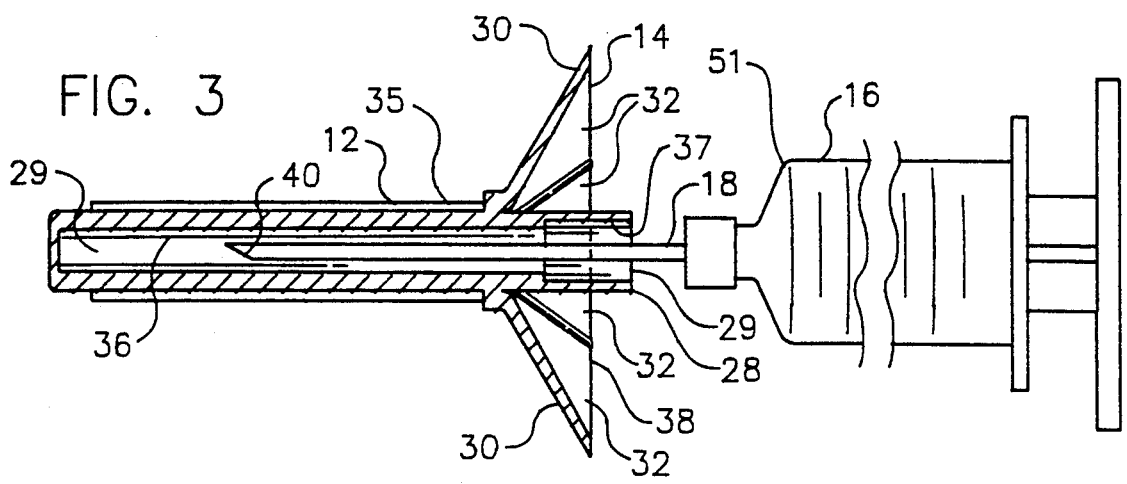
FIG. 3 is a cross-sectional view of the needle cap with integrally manufactured shield, showing a needle being recapped while attached to a syringe.

Turning now to FIG. 3, a cross sectional view of an integrally manufactured cap and shield is provided. Note how the ribs 30 extend outward from exterior sidewall 35 of cap 12. This view shows how needle 18 fits into the open end or annulus 29 of cap 12. The interior sidewall 36 of cap 12 may be provided with retaining means 37 (see also FIG. 3A below) to securely engage either the needle or the syringe when the capping operation is complete. As needles are available in a wide variety of configurations for attachment to syringes, the actual retaining means employed will have to be configured to secure the specific needle and/or syringe being employed. In addition, it can be clearly seen in this view that the panels 32 of shield 14 present a large frontal area 38 for catching the point 40 of needle 18.

FIG. 3A illustrates a separately manufactured shield, rather than the integrally manufactured shield first shown in FIG. 3 above. Here, ring 41 provides the structural support for ribs 30 and panels 32. The ring 41 may be slipped over an appropriately shaped portion of the exterior sidewall 35 of cap 12 until the ring is in a desire position with respect to the location of collapsed panels 32, as is more clearly set forth in FIG. 5 below.

Figure 4:
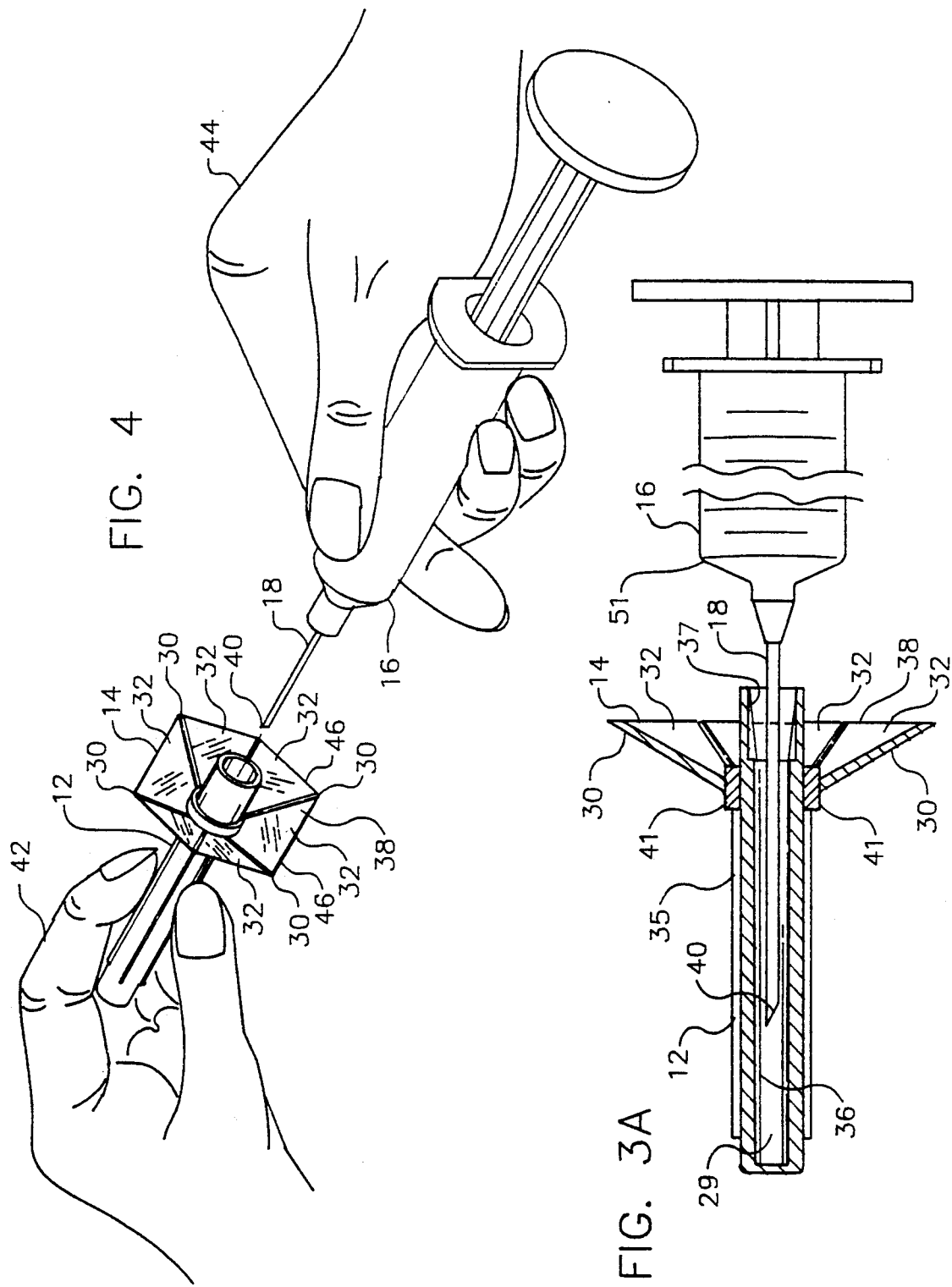
FIG. 4 is a perspective view of the cap and shield of the present invention being manipulated by a person while a needle is being re-capped.

The protective mechanism provided by shield 14 is more readily seen in FIG. 4. Here, the left hand 42 of a user is shown holding cap 12. Frontal area 38 of the shield 14 protects this left hand 42 from a stick by the point 40 of needle 18. As is clear from this FIG. 4, and as also seen in FIG. 2 above, unlike earlier collapsible shields known to us, the shield 14 of the present invention does not have any voids, holes, or open areas through which the point 40 of needle 18, shown in the right hand 44 of the user, could pass to stick the left hand 42 of the user.

Figure 5:
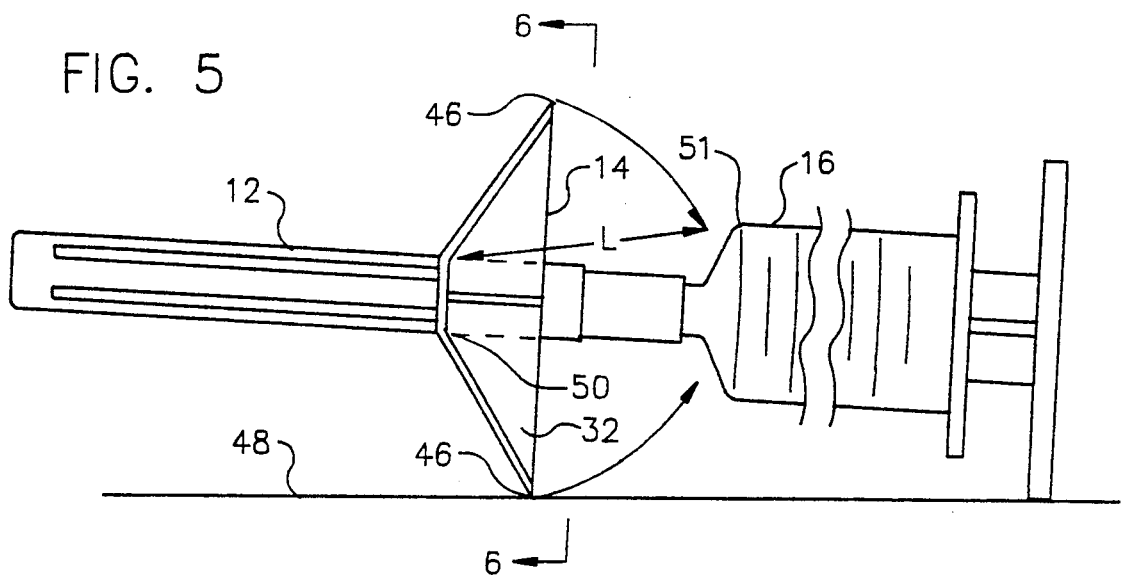
FIG. 5 is a side view of the cap and shield of the present invention setting in a stationary position on a flat surface after a needle and syringe have been re-capped.
Figure 6:
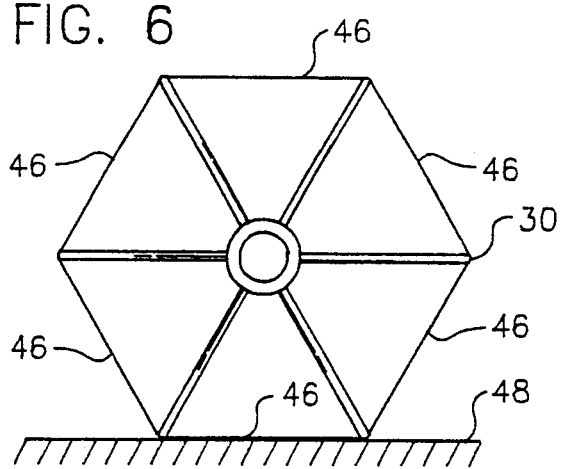
FIG. 6 is a view taken through the 6—6 line of FIG. 5, showing an end view of the flat edges of shield panels which enable the shield of the present invention to be placed on a flat surface in a stable position during use and re-use.

Also seen in FIG. 4, as well as in FIG. 2 above, are the flat outer edge segments 46 between ribs 30. These flat segments 46 are important since they enable the cap 12 and shield 14 to be securely positioned on a flat surface. This important property of stability in use is illustrated in FIG. 5. where a segment 46 fits flush against a flat surface 48, which surface may be such as a counter, table top, or tray. Also, this improved measure of stability as provided by flat edge segments 46 can be clearly seen in FIG. 6.

Referring back to FIG. 2, it can be seen that panels 32 each have an interior edge or central segment 50 which attaches to cap 12 (via way of ring 34 if provided). Also, panels 32 have a first internal edge portion 52 which joins a first rib 30, and a second internal edge portion 54 which joins a second rib 30, in an integral and seamless manner.

Returning now to FIG. 5, also illustrated is an important configuration detail of the collapsible design of the present invention. Panels 32 should be of a length L such that when their interior edge 50 is positioned on the cap 12 in the operating location, the outer edge 46 of the panel does not extend over shoulder 51 of syringe 16 so as to impair the packing efficiency. For many applications, a length L in the range of 2 to 3 cm would be suitable, however, the actual length L may be varied upward or downward beyond this range as necessary for a particular size needle and syringe.

Figure 7:
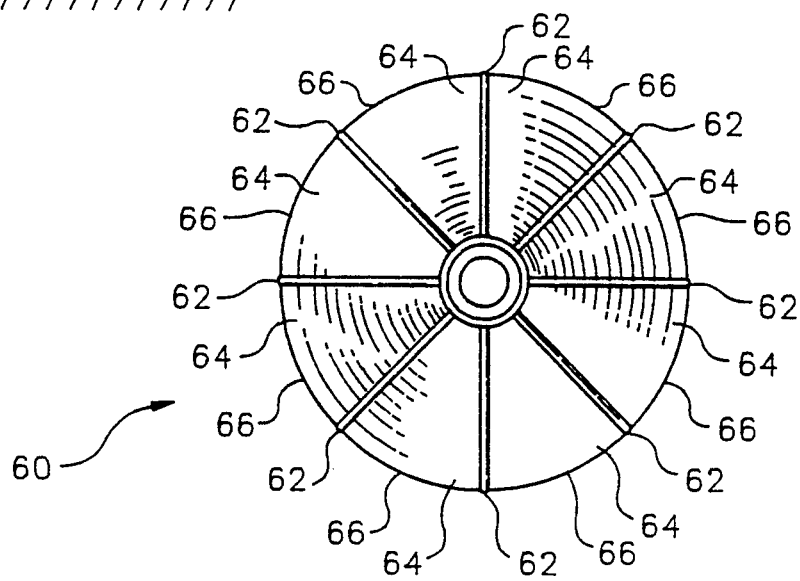
FIG. 7 is an end view of a second embodiment of the present invention wherein the collapsible shield is configured in a circular design, wherein the edges of the panels of the shield are rounded.

Turning now to FIG. 7, there is illustrated an alternate embodiment of the collapsible shield of the present invention. A shield 60 has ribs 62 and panels 64. The panels have rounded outer edge segments 66. While this embodiment does not provide the positioning stability of the flat edge segments 46 of the earlier illustrated embodiment, this alternate embodiment nevertheless offers the advantage of collapsible construction.

Also, note in FIG. 7 that an octagonal design is shown in this shield 60, whereas a hexagonal design is shown in the first illustrated shield 14 described above. Any polygonal shaped shield 14 with flat outer edge segments 46 will provide the desired positioning stability, and the exact shape chosen is up to the convenience of the designer.

Figure 8:
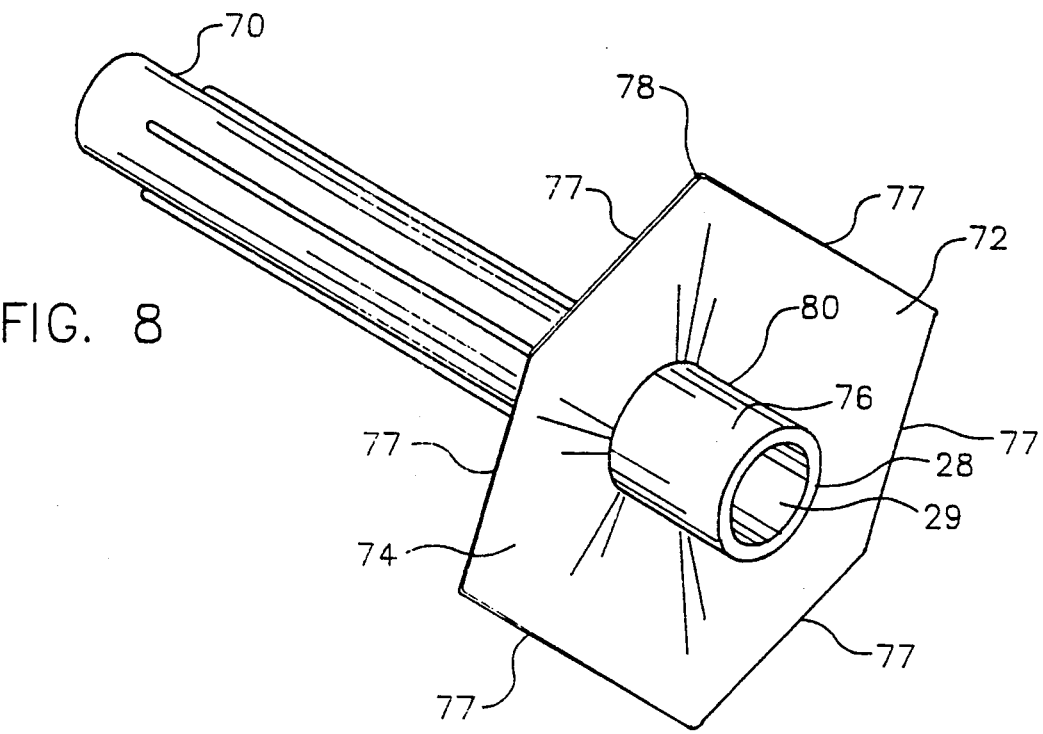
FIG. 8 is a perspective view of a third embodiment of the present invention wherein the collapsible shield is manufactured in a continuous manner, without discrete panels.

In FIG. 8, yet another embodiment of our invention is illustrated. A cap 70 is shown with a continuous shield 72. Rather than being constructed with panels for strength as above, the shield 72 is constructed of a continuous shaped plastic portion 74 which protrudes from the external surface 76 of cap 70. In this embodiment, it is not necessary to provide ribs, ridges, or channels to provide the ability of the device to fold for packaging, although when rolled for packing, creases will naturally appear. The key is to provide materials of construction so that such seams do not affect the expansion to full size and protection when in the open position shown in this FIG. 8. While it is most desirable to provide flat perimeter surfaces 77 so as to provide stability to the device when placed on a flat surface, this basic configuration could also be constructed with a rounded perimeter.

Figure 9:
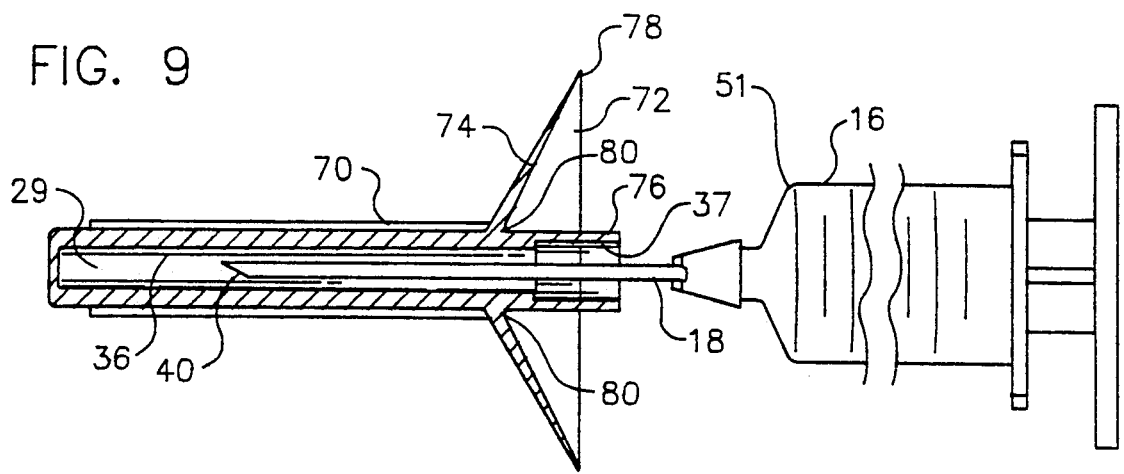
FIG. 9 is a cross-sectional view of the third embodiment of the present invention as first set forth in FIG. 8, now illustrating the technique of increasing the thickness of the shield from tip to root.

As can be seen in the FIG. 9, a cross sectional view of the embodiment first set forth in FIG. 8 shows an integrally formed cap 70 and shield 72. The protrusion 74 has a thickness T which increases from tip 78 toward root 80. When the the shield 72 is integrally formed with cap 70, root 80 is attached to and made a part of the continuous mold of the cap 70. However, it will be recognized that a continuous shield similar to shield 72 may be constructed separately as will be obvious by reference to FIG. 3A above. In any event, the strength to urge the tip 78 outward away from the external surface 72 of cap 70 is provided by the material comprising the root 80. While a desirable thickness T at root 80 may be in the range of 1 to 2 mm, more or less thickness T may be desirable for larger or smaller needles than is needed for a common size cap 70 which is shown essentially full size in this FIG. 9.

Thus, it can be seen that we have developed and have set forth herein an exemplary needle cap and shield. The cap and shield is lightweight, and is collapsible thus capable of easily being packaged and shipped without taking up undue space. The shield may be manufactured separately from, or preferably, integrally with, the needle cap.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalences of the claims are therefore intended to be embraced therein.

We claim:

1. A needle cap and shield, comprising:
    (a) a housing comprising
        (i) a sidewall, said sidewall having an interior and an exterior, and
        (ii) a frontal opening, said opening adapted to receive a needle;
    (b) a continuous flexible shield portion, said portion extending upward away from said exterior sidewall, said continuous shield portion further comprising a plurality of spaced panels extending upward from said exterior sidewall, wherein adjacent panels have interior edges therebetween, and wherein said interior edges are shaped for defining generally stiff projections to integrally support the said panels out of contact with said exterior sidewall.

2. The needle cap and shield as recited in claim 1, wherein said edges comprise ribs projecting from said exterior sidewall of said housing toward an outer edge of said panels.

3. The needle cap as recited in claim 2, wherein said ribs are fabricated of a material which allows said ribs to extend outward from a compressed, shipping position to an extended, protective position.

4. A needle cap and shield as set forth in claim 3, wherein the shield portion further comprises:
a plurality of panels each having a central edge, said panels being affixed to said external surface portion of said cap along aid central edges;
wherein said ribs extend outward from said cap portion upon release of said ribs from their compressed, shipping position, and
wherein said panels are progressively more tautly pulled outward by said ribs as said ribs extend outwardly away from said cap portion, so that said panels form a protective barrier between a first, needle receiving end of said cap and a second, handling end of said cap, said handling end being adapted to be gripped by a user.

5. The needle cap as recited in claim 2, wherein said ribs are equally spaced.

6. The needle cap as recited in claim 2, wherein said ribs project the entire distance between said exterior sidewall and said outer edge.

7. The needle cap as recited in claim 2:
(a) wherein said rib portions include central ends, said central ends being positioned within an optimum range position along said exterior sidewall, and
(b) wherein said rib portions have a suitable length L, so that when said rib portions of length L are affixed to said housing at said optimum endpoint range position, said ribs do not impair the ability of a needle to engage said cap when said rib portions are in their compressed, shipping position.

8. The needle cap and shield as recited in claim 1, wherein said shield portion further includes a ring portion, said ring integrally formed with said external surface portion.

9. The needle cap with shield as recited in claim 8, wherein said shield portion is separable from said cap portion, and where said shield portion may be affixed to said cap portion at a desired position along said longitudinal axis.

10. A needle cap with shield as set forth in claim 1, wherein the shield portion further comprises a plurality of panels, each panel having a central edge, said panels being affixed along said central edges to said housing;
wherein said integral supports extend outward from said housing upon release of said integral supports from their compressed, shipping position; and
wherein said panels are progressively more tautly pulled outward by said integral supports as said integral supports extend outwardly away from said housing, so that said panels form a protective barrier between a first, needle receiving end of said cap and a second, handling end of said cap which is adapted to be gripped by a user.

11. A needle cap with shield as set forth in claim 8, wherein the shield portion further comprises
a plurality of panels each having a central edge, said panels being affixed to said ring portion of said shield along said central edges;
wherein said ribs extend outward from said ring portion upon release of said ribs from their compressed, shipping position, and
wherein said panels are progressively more tautly pulled outward by said ribs as said ribs extend outwardly away from said cap portion, so that said panels form a protective barrier between a first, needle receiving end of said cap and a second, handling end of said cap which is adapted to be gripped by a user.

12. The needle cap of claims 10 or 11, wherein said panels each having an external edge, and wherein said external edge is flat, so that said cap does not tend to move when placed on a flat surface.

13. The needle cap of claim 2 wherein said integral supports, when said cap is in said expanded, protective position, provide a stable positioning means so that said cap does not tend to move when placed on a flat surface.

14. The needle cap of claim 1, wherein said continuous shield is shaped for integrally defining generally stiff projections of variable thickness for supporting the said shield out of contact with the exterior sidewall.

15. The needle cap as recited in claim 14, wherein said continuous shield has a tip and root, and wherein said shield has a thickness T which increases from the tip of the root.

16. The needle cap as recited in claim 1, wherein said shield includes a plurality of flat perimeter surfaces.

17. The needle cap as recited in claim 1, wherein said shield is fabricated of a material which allows said panel to extend outward from a compressed, shipping position to an extended, protective position.

18. The needle cap of claim 1, wherein said shield has an external edge, and wherein said external edge is rounded, so that said cap may move when placed on a flat surface.

19. The needle cap and shield as recited in claim 2, wherein a tab portion is provided to secure said shield portion in said compressed, shipping position.

20. The needle cap and shield as set forth in claim 19, wherein said tab is provided in a bright or fluorescent color.

21. The needle cap and shield as set forth in claim 19, wherein said tab is thermowelded to a rib.

* * * * *